(12) United States Patent
Powell

(10) Patent No.: US 10,874,144 B2
(45) Date of Patent: Dec. 29, 2020

(54) ELECTRONIC VAPOUR GENERATING DEVICE

(71) Applicant: XOLO LIMITED, London (GB)

(72) Inventor: Taman Powell, London (GB)

(73) Assignee: XOLO LIMITED, London (GB)

(*) Notice: Subject to any disclaimer, the term of this patent is extended or adjusted under 35 U.S.C. 154(b) by 295 days.

(21) Appl. No.: 15/578,856

(22) PCT Filed: May 31, 2016

(86) PCT No.: PCT/GB2016/051586
§ 371 (c)(1),
(2) Date: Dec. 1, 2017

(87) PCT Pub. No.: WO2016/193705
PCT Pub. Date: Dec. 8, 2016

(65) Prior Publication Data
US 2018/0295883 A1  Oct. 18, 2018

(30) Foreign Application Priority Data
Jun. 3, 2015 (GB) .................................. 1509590.4

(51) Int. Cl.
*A24F 47/00* (2020.01)
*A61M 15/06* (2006.01)
(Continued)

(52) U.S. Cl.
CPC .............. *A24F 47/008* (2013.01); *A24F 7/00* (2013.01); *A61M 11/042* (2014.02);
(Continued)

(58) Field of Classification Search
CPC ..................................................... A61M 15/06
(Continued)

(56) References Cited

U.S. PATENT DOCUMENTS

| 2006/0102175 A1 | 5/2006 | Nelson |
| 2007/0045288 A1 | 3/2007 | Nelson |
| 2013/0042865 A1 | 2/2013 | Monsees et al. |

FOREIGN PATENT DOCUMENTS

| CN | 203986121 U | 12/2014 |
| WO | 0050111 A1 | 8/2000 |

(Continued)

*Primary Examiner* — Michael H. Wilson
*Assistant Examiner* — Katherine A Will
(74) *Attorney, Agent, or Firm* — Joseph C. Zucchero; Carolyn S. Elmore; Elmore Patent Law Group, P.C.

(57) ABSTRACT

An electronic vapour generating device and cartridge for use therein is disclosed. The device comprises a housing defining a chamber for receiving a cartridge for holding a liquid for atomisation, and a power source for providing electrical power to an atomiser for atomising the liquid. The device further comprises an actuator which is reconfigurable between a first state in which the actuator electrically isolates the atomiser from the power source and a second state for enabling the generation of the vapour. The device further comprises a mouthpiece which is arranged to fluidly couple with the atomiser for communicating the vapour out from the device for inhalation by a user and which is slidably coupled to the housing. The mouthpiece is reconfigurable between a stowed configuration and an operative configuration and reconfiguration of the mouthpiece between the stowed and operative configuration is arranged to reconfigure the actuator between the first and second state.

11 Claims, 6 Drawing Sheets

(51) Int. Cl.
*A61M 15/00* (2006.01)
*A61M 11/04* (2006.01)
*A24F 7/00* (2006.01)
*A61M 16/00* (2006.01)

(52) U.S. Cl.
CPC ........ *A61M 15/0023* (2014.02); *A61M 15/06* (2013.01); *A61M 2016/0024* (2013.01); *A61M 2205/50* (2013.01); *A61M 2205/8206* (2013.01); *A61M 2205/8237* (2013.01)

(58) Field of Classification Search
USPC ........................................................ 131/329
See application file for complete search history.

(56) References Cited

FOREIGN PATENT DOCUMENTS

| | | |
|---|---|---|
| WO | 2012114322 A1 | 8/2012 |
| WO | 2014066730 A1 | 5/2014 |
| WO | 2015128667 A1 | 9/2015 |
| WO | 2016026105 A1 | 2/2016 |

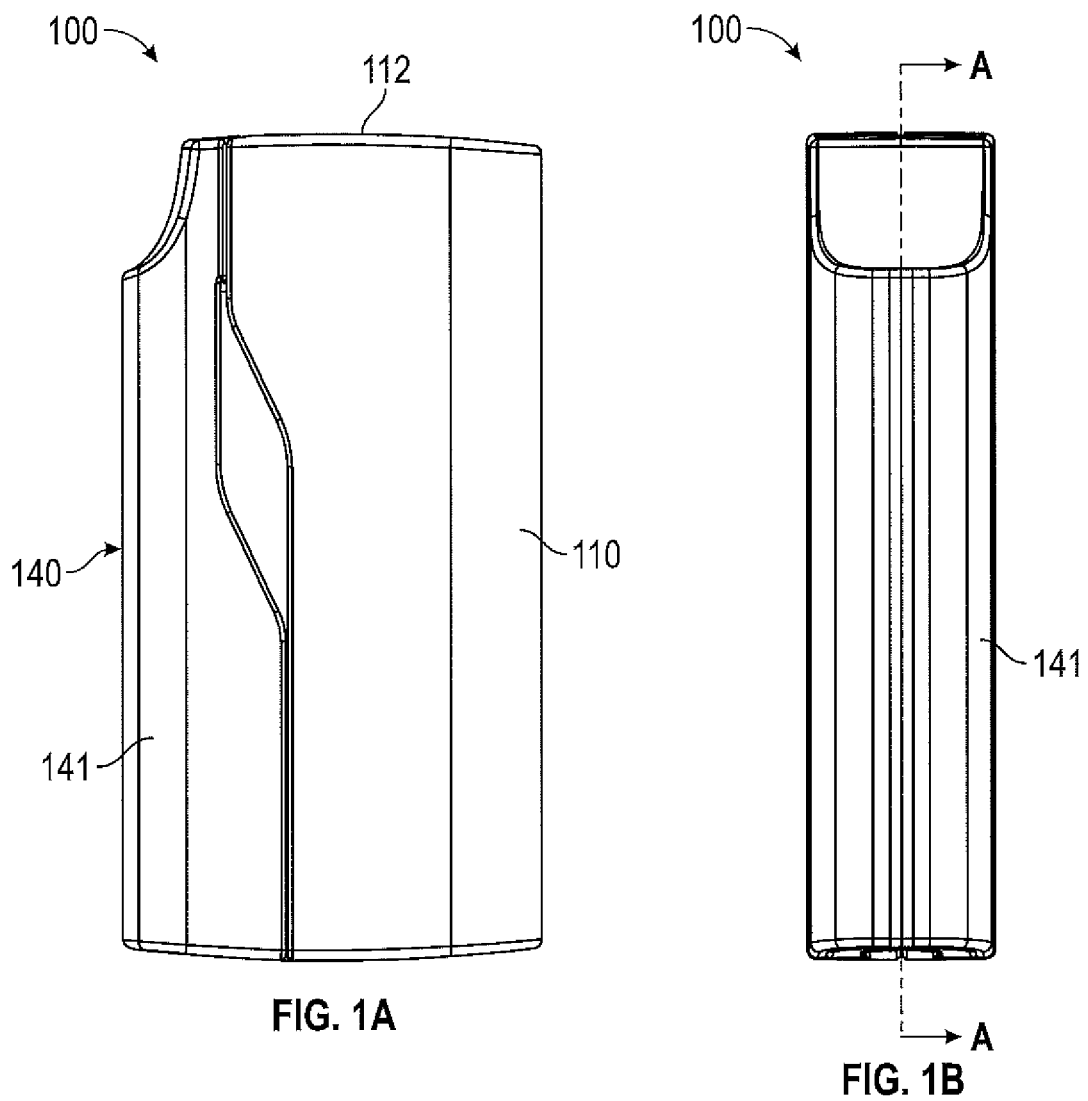
FIG. 1A
FIG. 1B
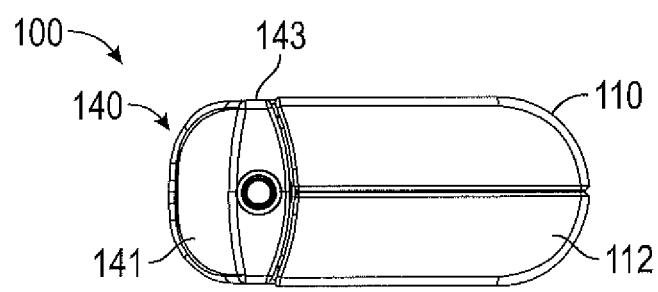
FIG. 1C

ELECTRONIC VAPOUR GENERATING DEVICE

RELATED APPLICATIONS

This application is a national phase application of International Application No. PCT/GB2016/051586, which designated the United States and was filed on May 31, 2016, published in English, which claims priority to Great Britain Application No. 1509590.4, filed on Jun. 3, 2015. The entire teachings of the above applications are incorporated herein by reference.

The present invention relates to an electronic vapour generating device and a cartridge for an electronic vapour generating device.

Nicotine is a well-known constituent of cigarettes which is responsible for cigarette addiction. In addition to nicotine however, cigarettes contain harmful chemicals, such as tar, which can seriously affect an individual's health. In an endeavour to wean individuals from cigarette use, so-called electronic cigarettes have been developed which provide a user with a nicotine fix, without the harmful chemicals associated with traditional cigarettes.

Electronic cigarettes (or vaping products) typically comprise a liquid reservoir containing the consumable liquid, commonly known as "E-liquid", which may contain nicotine, and an atomiser which is arranged to atomise the liquid to create a vapour which the user can inhale via a mouthpiece. Such vaping products were originally developed as a way to provide nicotine in a sensorially pleasing inhalable vapour, but without the associated harms associated with smoking. Recent market trends have shown that experienced users of vaping products tend towards higher powered devices than those which are generally available from non-specialist retailers. These devices tend to be large, cumbersome and hard to use by the novice user.

We have now devised an improved electronic vapour generating device.

In accordance with the present invention, there is provided an electronic vapour generating device, the device comprising a housing defining a chamber for receiving a cartridge for holding a liquid for atomisation, and a power source for providing electrical power to an atomiser for atomising the liquid to generate a vapour, the device further comprising an actuator which is reconfigurable between a first state in which the actuator electrically isolates the atomiser from the power source and a second state for enabling the generation of the vapour, the device further comprising a mouthpiece which is arranged to fluidly couple with the atomiser for communicating the vapour out from the device for inhalation by a user, wherein the mouthpiece is reconfigurable between a stowed configuration and an operative configuration.

In an embodiment, the reconfiguration of the mouthpiece between the stowed and operative configuration is arranged to reconfigure the actuator between the first and second state in which the atomiser and power source are electrically coupled. In an alternative embodiment, the reconfiguration of the mouthpiece between the stowed and operative configurations is arranged to reconfigure the actuator between a first state in which the actuator electrically isolates the atomiser from the power source and a standby state in which the actuator is electrically couplable with the power source, In an embodiment, the mouthpiece is slidably coupled to the housing. In an alternative embodiment, the mouthpiece may be pivotally or rotatably coupled to the housing.

Advantageously, the reconfigurable nature of the slidable mouthpiece, married with the actuation of the device, provides for a more compact vapour generating device.

In an embodiment, the actuator comprises a switch which is reconfigurable between an open and closed state in accordance with the reconfiguration of the mouthpiece between the stowed and operative configurations.

In a further embodiment, the actuator comprises a first switching assembly and a second switching assembly. Preferably the first switching assembly is reconfigurable between an open and closed state in accordance with the reconfiguration of the mouthpiece between the stowed and operative configurations and the second switching assembly is reconfigurable between an open and closed state in dependence of a detected pressure within the mouthpiece.

In an embodiment, the mouthpiece is arranged to fluidly couple with the atomiser in the stowed and operative configurations.

In an embodiment, a distal end of the mouthpiece is arranged to extend substantially flush with a periphery of the housing when the mouthpiece is arranged in the stowed configuration. The distal end of the mouthpiece is preferably disposed away from the housing when the mouthpiece is arranged in the operative configuration.

In an embodiment, the mouthpiece is reconfigurable between a stowed configuration, an operative configuration and a release configuration. In the release configuration, the mouthpiece may be separated from the housing, to permit a cartridge of liquid to be replaceably positioned within the chamber, and subsequently coupled with the housing.

In an embodiment, the cartridge is removably insertable within a vapour generating device. The cartridge preferably comprises a receptacle for retaining the liquid for atomisation and an atomiser disposed within the receptacle for atomising the liquid. In an embodiment, the cartridge further comprises a duct communicatively coupled with the atomiser for communicating vapour generated by the atomiser out from the cartridge.

In an embodiment, the mouthpiece is fluidly coupled to the atomiser via a connecting pipe which is sealingly and slidably coupled to the duct of the cartridge, such that the pipe is arranged to slide relative to the duct as the mouthpiece reconfigures between the stowed and operative configurations.

In an embodiment, the atomiser and duct are preferably orientated along a common axis.

In an embodiment, the atomiser comprises a plurality of channels formed in an outer wall thereof for communicating liquid disposed within the receptacle into the atomiser. The cartridge further comprises a sleeve which shrouds at least a portion of the atomiser. The sleeve comprises a plurality of apertures which are preferably alignable with the channels to permit the liquid to pass into the atomiser.

In an embodiment, the duct is preferably coupled to the sleeve and the sleeve is arranged to move relative to the atomiser by manipulating the duct.

In an embodiment, the cartridge further comprises a docking station for providing electrical communication of the atomiser with the electronic vapour generating device. The docking station may further comprise a locating member, such as magnet for suitably locating the cartridge within the electronic vapour generating device.

In an embodiment, the device further comprises a potentiometer for varying the voltage applied by the power source across the atomiser. It is found that the amount of vapour generated by the atomiser is related to the voltage applied across the atomiser, and as such a user can tailor the amount of vapour generated to suit their preference by varying the voltage.

Preferably, the power source comprises a battery arrangement, such as a rechargeable battery arrangement. The device further comprises an electrical port disposed in the housing for receiving an electrical connector for electrically coupling the power source with an external power supply, such as a mains voltage supply.

In an embodiment, the device further comprises a timer and a processor for controlling the operation of the atomiser and for monitoring the length of time for which the mouthpiece remains in the second configuration. The processor may be arranged to electrically isolate the atomiser from the power source following a pre-determined time, even with the mouthpiece arranged in the operative configuration. Preferably, the pre-determined time comprises a time in the range 5-10 seconds.

In an embodiment, the device further comprises a slider mechanism for slidably coupling the mouthpiece to the housing. The slider mechanism preferably comprises biasing means for biasing the mouthpiece in the stowed configuration and separately the operative configuration, such that a user is required to overcome a threshold force in reconfiguring the mouthpiece between the stowed and operative configuration. The biasing means may comprise one or more springs and/or magnets for biasing the mouthpiece in the stowed and operative configurations.

According to a second aspect of the present invention, there is provided a cartridge for providing liquid for use in an electronic vapour generating device, the cartridge comprising a receptacle for retaining the liquid and an atomiser disposed within the receptacle for atomising the liquid, the cartridge further comprising a duct fluidly coupled with the atomiser for communicating vapour generated within the atomiser out from the cartridge.

In an embodiment, the duct is arranged to slidingly couple with a connecting pipe of an electronic vapour generating device, such that the connecting pipe can slide, preferably in sealing contact with the duct, relative to the duct.

In an embodiment, the atomiser and duct are preferably orientated along a common axis.

In an embodiment, the atomiser comprises a plurality of channels formed in an outer wall thereof for enabling liquid disposed within the receptacle to pass into the atomiser. The cartridge further comprises a sleeve which shrouds at least a portion of the atomiser. The sleeve comprises a plurality of apertures which are preferably alignable with the channels to permit the liquid to pass into the atomiser.

In an embodiment, the duct is preferably coupled to the sleeve and the sleeve is arranged to move relative to the atomiser by manipulating the duct.

In an embodiment, the cartridge further comprises a docking station for providing electrical communication of the atomiser with an electronic vapour generating device. The docking station may further comprise a locating member, such as magnet for suitably locating the cartridge within the electronic vapour generating device.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments.

Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

The invention may be performed in various ways, and, by way of example only, embodiments thereof will now be described, reference being made to the accompanying drawings in which:

FIG. 1a is a front view of an electronic vapour generating device according to an embodiment of the present invention;

FIG. 1b is a side view of the electronic vapour generating device illustrated in FIG. 1a;

FIG. 1c is a top view of the electronic vapour generating device illustrated in FIG. 1a;

Figure 2A:
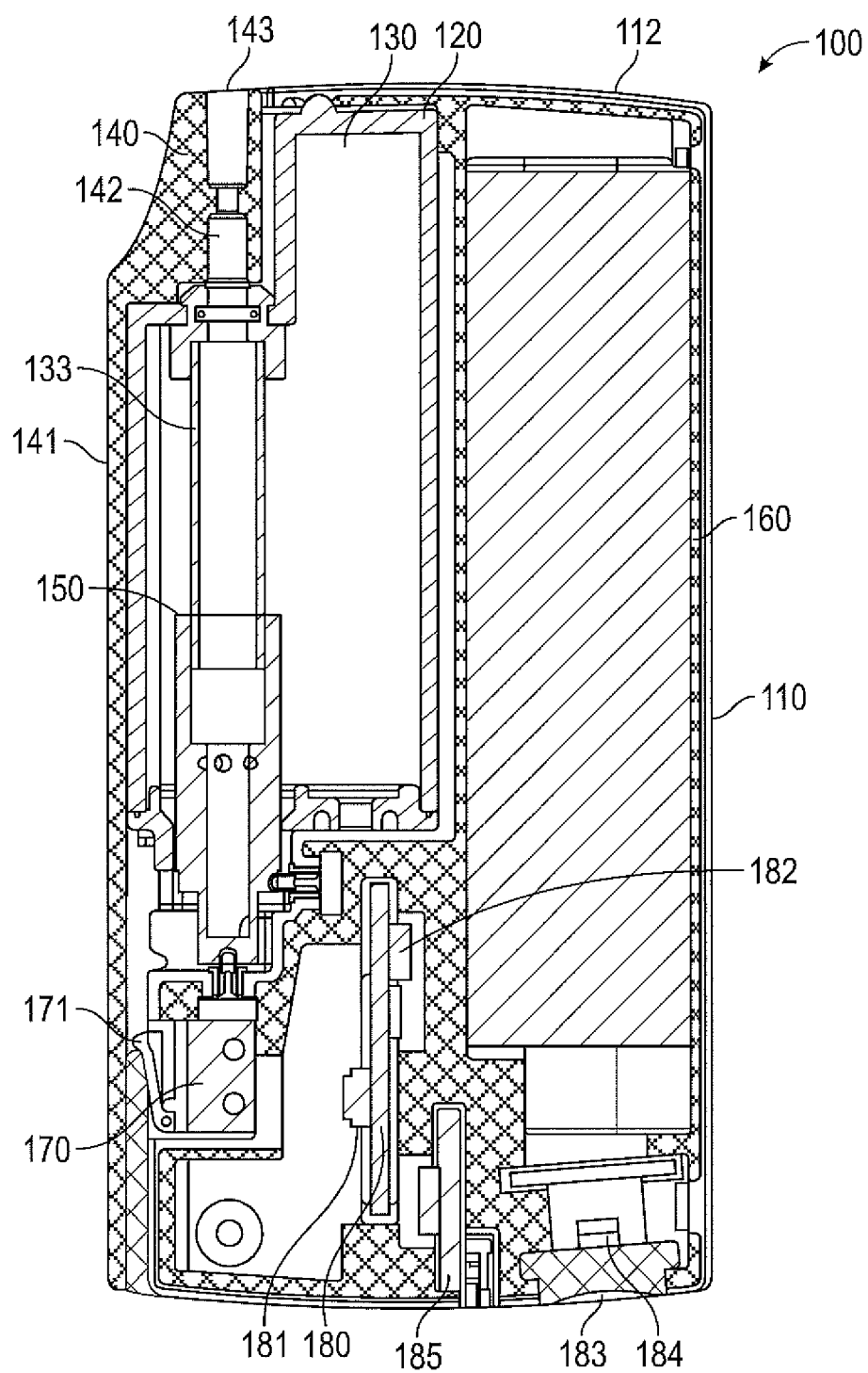
FIG. 2a is a schematic sectional view of a first embodiment of an electronic vapour generating device illustrated in FIG. 1, taken along line A-A of FIG. 1b.

Referring to FIGS. 1 and 2a of the drawings, there is illustrated an electronic vapour generating device 100 according to a first embodiment of the present invention. The device comprises a housing 110 which may be formed of a rigid plastics material or a metal, such as aluminium. The housing 110 provides a protective case for several of the device components and defines a chamber 120 therein for receiving a replaceable cartridge 130, which is arranged to retain a liquid from which the vapour is generated.

The device 100 comprises a mouthpiece 140 which in the illustrated embodiment is slidably coupled along a lateral side edge 111 of the housing 110. However, in an alternative embodiment which is not illustrated, the mouthpiece may be pivotally or rotatably coupled to the housing 110. Referring to the illustrated embodiment in FIGS. 1 and 2a, the mouthpiece 140 extends longitudinally of the housing 110 and is slidable along the lateral side edge 111, in a direction which is substantially parallel to a longitudinal axis of the device 100. The mouthpiece 140 is reconfigurable between a stowed configuration and an operative configuration and comprises an external shell 141, which may be formed of a rigid plastics material or a metal, such as aluminium, similar to the housing 110. The mouthpiece shell 141 is shaped to compliment the shape of the housing 110, such that the mouthpiece shell 141 and housing collectively define a substantially cuboid shape when the mouthpiece 140 is arranged in the stowed configuration. When configured in the operative configuration, a distal end of the mouthpiece 140 is arranged to extend away from the housing 110 and is disposed above an upper region 112 of the housing.

Figure 3A:
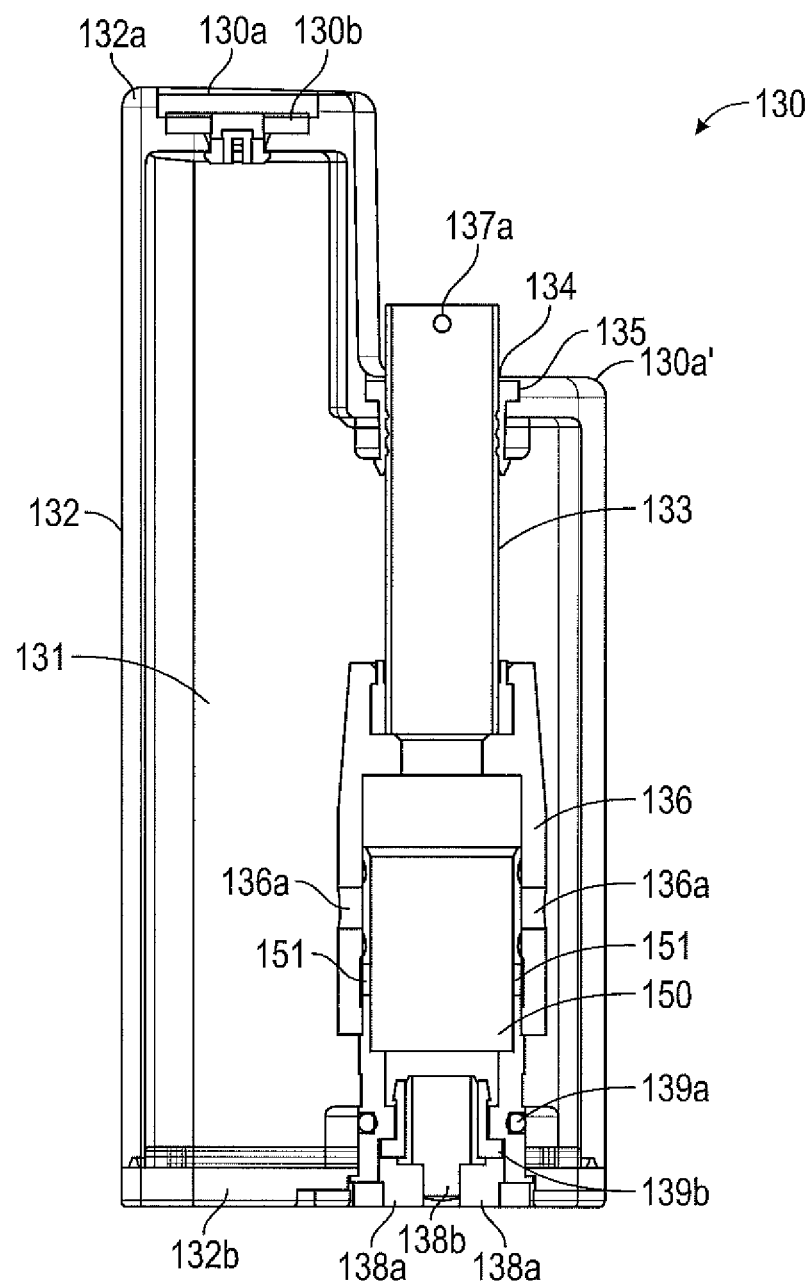
FIG. 3a is a sectional view through a cartridge with the duct arranged in a raised configuration.
Figure 3B:
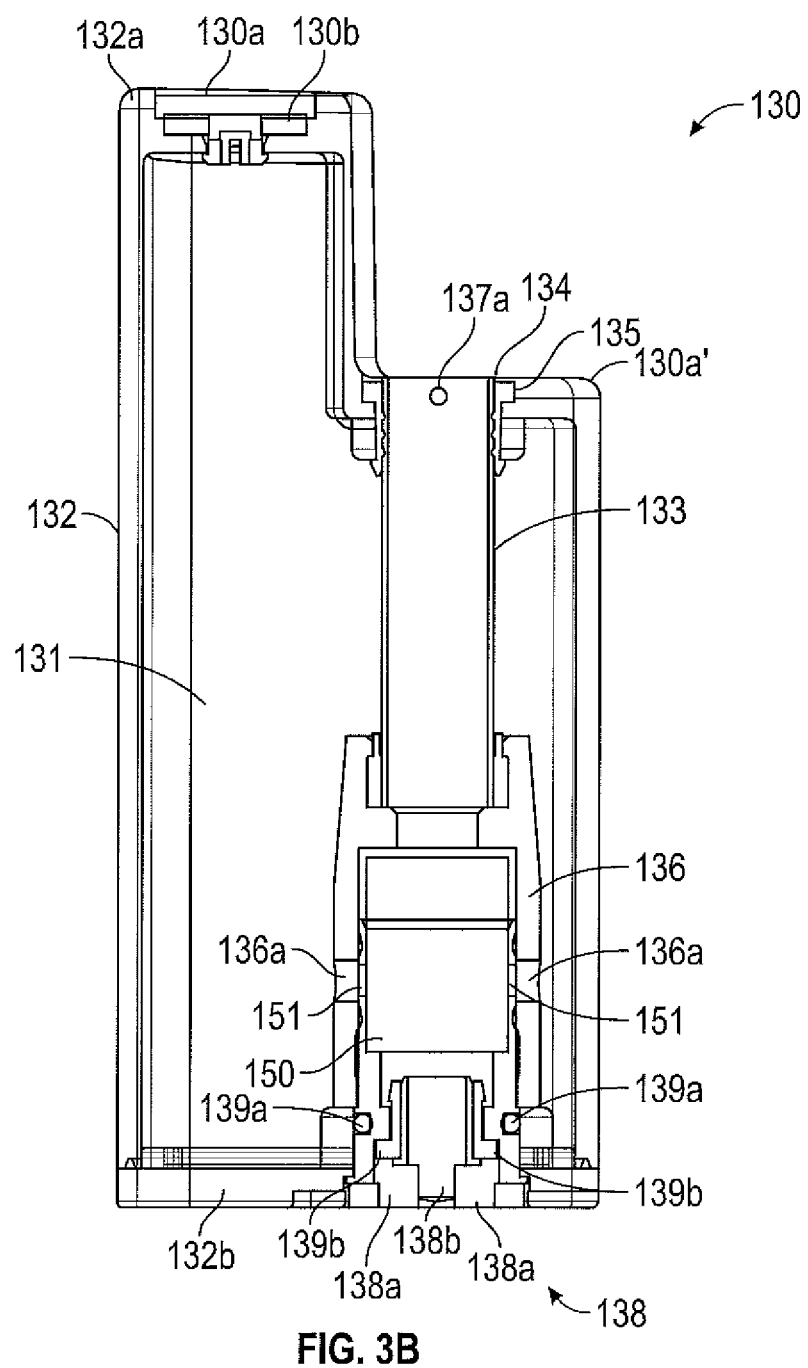
FIG. 3b is a sectional view through a cartridge with the duct arranged in a lowered configuration.

Referring to FIGS. 3a and 3b of the drawings, there is illustrated a cartridge 130 according to an embodiment of the present invention for providing liquid for use in an electronic vapour generating device, such as the device 100 mentioned above (or the device 200 of the second embodiment mentioned below). The cartridge 130 comprises a receptacle 131 defined by an outer wall 132 of the cartridge 130, for retaining the liquid from which the vapour is generated. The cartridge 130 may be filled via a removably securable cap 130a disposed in an upper wall portion 132a of the cartridge 130. The cap 130a may be arranged to screw/unscrew into/from the upper wall portion 132a for example, and comprises a seal 130b disposed at the underside of the cap 130a for providing a sealing coupling with the upper wall portion 132a. The cartridge 130 further comprises an atomiser 150 disposed within the receptacle 131 for atomising the liquid in generating the vapour. The atomiser 150 comprises a substantially cylindrical cross-sectional outer wall, and extends from a base 132b of the cartridge 130. An upper portion of the atomiser 150 is fluidly coupled with a duct 133 which extends upwardly from the atomiser 150 substantially along an axis of the atomiser 150, and comprises an open distal end which is slidingly and sealingly coupled within a port 134 formed in an upper wall portion 132a' of the wall 132 of the cartridge 130, via a collar seal 135 which extends around the duct 133. The duct 133 is arranged to communicate vapour generated within the atomiser 150 out from the receptacle 131 and into the mouthpiece 140 for inhalation by a user.

In the illustrated embodiment, the cartridge 130 comprises a substantially cuboid shape, however, the upper wall portion 132a is vertically displaced above upper wall portion 132a', of the cartridge, such that the upper wall comprises a stepped profile.

The atomiser 150 comprises a plurality of channels 151 formed in the outer wall thereof, which are angularly separated around the outer wall, for communicating liquid from within the receptacle 131 into the atomiser 150. However, prior to the initial use of the cartridge 130 within the vapour generating device 100 (or vapour generating device 200—see below), it is desirable to prevent the liquid from entering the atomiser 150. It is preferable to maintain the liquid in a sealed environment within the receptacle 131 to preserve the integrity of the liquid, such as during periods where the cartridge 130 is held in storage. Accordingly, the cartridge 130 further comprises a sleeve 136 which is arranged to shroud at least a portion of the atomiser 150. The sleeve 136 is coupled at an upper region thereof to the duct 133 and comprises a plurality of apertures 136a formed therein and angularly separated around the sleeve 136.

Prior to the initial use of the cartridge 130, a distal end of the duct 133 extends out from the receptacle 131 via the port 134 and the sleeve 136 is disposed in a raised configuration relative to the atomiser 150, such that the channels 151 formed within the atomiser 150 are closed by the sleeve 136. In this configuration, the sleeve 136 prevents liquid from entering the atomiser 150 and thus effectively seals the liquid within the receptacle 131. When a user wishes to insert the cartridge 130 within the vapour generating device 100, the user first presses upon the distal end of the duct 133 to cause the duct 133 to pass into the receptacle 131. At the same time, this causes the sleeve 136 to slide down an outer side of the atomiser 150. When the duct 133 has been fully inserted, a barb 137 (as illustrated in FIG. 3b of the drawings) formed upon the cartridge wall 132 is arranged to snap-locate within an aperture 137a formed within the distal end of the duct 133 to lock the duct 133 and thus the sleeve 136 in a lowered configuration in which the apertures 136a in the sleeve 136 become aligned with the channels 151 within the atomiser 150. In this configuration, the liquid can pass into the atomiser 150 via the aligned apertures 136a and channels 151 for atomisation.

The cartridge 130 further comprises a docking station 138 formed at a base of the cartridge 130. The docking station 138 is disposed at an underside of the atomiser 150 and comprises an internal volume which is sealed from an interior of the receptacle 131 via an o-ring seal and collar seal 139a, 139b. The docking station comprises a plurality of electrical contactors 138a which provide an electrical path into the cartridge 130, and particularly to electrical connections (not shown) of the atomiser 150 so that electrical power can be supplied to the atomiser 150. The docking station 138 further comprises a locating member, such as a magnet 138b which is arranged to interact with a magnet (not shown) disposed within the chamber 120, for suitably aligning and locating the cartridge 130 in the chamber 120.

The mouthpiece 140 is fluidly coupled with the duct 133 via a connecting pipe 142 which is rigidly coupled at a proximal end thereof to an opening 143 disposed, in use, at an upper region of the mouthpiece 140. A distal end of the pipe 142 extends in sliding and sealing contact within an interior of the duct 133, such that vapour generated within the atomiser 150 can pass out from the mouthpiece 140 via the duct 133 and pipe 142.

The atomiser 150 is powered by a power source 160, such as a rechargeable battery arrangement disposed within the housing 110, via an actuator, such as a switch 170 also disposed within the housing 110. The switch 170 comprises a reconfigurable arm 171 which can rotate to open and close the switch 170 and thus electrically couple and decouple (namely isolate) the atomiser 150 with/from the battery arrangement 160. The rotation of the arm 171 is effected by the movement of the mouthpiece 140 along the lateral side edge 111 of the housing 110, such that in the stowed configuration, the switch 170 is arranged to take up an open state in which operation of the atomiser 150 is prevented and the device is "off". However, as the mouthpiece 140 reconfigures to the operative configuration, the switch 170 is arranged to reconfigure to a closed state to electrically couple the battery arrangement 160 with the atomiser 150 and thus place the device in an "on" state.

The mouthpiece 140 is slidably coupled to the device housing 110 via a slider mechanism (not shown). The mechanism comprises biasing means (not shown) which is arranged to bias the mouthpiece 140 in the stowed and operative configurations such that a user is required to overcome a threshold force in reconfiguring the mouthpiece 140. The bias on the mouthpiece 140 may be provided by one or more springs (not shown), for example, whereby the reconfiguration of the mouthpiece 140 requires the one or more springs (not shown) to compress for example, before subsequently recovering to their natural length as the mouthpiece 140 adopts the stowed or operative configuration. Alternatively, or in addition thereto, the bias may be provided by one or more magnets (not shown), whereby the reconfiguration of the mouthpiece 140 causes a progressive increase in the force created by magnetic repulsion between magnets (not shown), up to a threshold position. However, as the mouthpiece 140 moves beyond the threshold position, the magnetic repulsive force is arranged to bias the mouthpiece 140 to the desired configuration.

In an embodiment, the mouthpiece 140 is further reconfigurable to a release configuration, which is achieved by sliding the mouthpiece 140 beyond the operative configuration. In this configuration, the mouthpiece 140 can uncouple from the lateral edge 111 of the housing 110 to enable a cartridge 130 to be replaced/inserted within the chamber 120. The mouthpiece 140 may then be further coupled with the housing 110 and reconfigured to the operative or stowed configuration, as desired.

The vapour generating device 100 further comprises a printed circuit board 180 comprising a timer 181 and a processor 182 for controlling operation of the atomiser 150 and for monitoring the activation time of the atomiser 150, namely the time occupied by the mouthpiece 140 in the operative configuration. The device 100 further comprises a dial 183 disposed within the housing 110 which is accessible to user. The dial 183 is coupled with a potentiometer 184 which is arranged to control the voltage applied by the battery arrangement 160 across the atomiser 150. It is found that the amount of vapour generated by the atomiser 150 is related to the voltage applied across the atomiser 150, and as such, a user can tailor the amount of vapour generated to suit their preference by varying the voltage. It is also envisaged that the device may comprise a temperature sensing device (not shown) for monitoring the temperature of the atomiser 150. It is found that the atomiser 150 can get hot during prolonged periods of operation and the temperature sensing device is arranged to output a signal to the switch 170 in dependence of the sensed temperature to cause the switch 170 to reconfigure from a closed state to an open state. For example, in situations where the temperature sensing device (not shown) detects a temperature above a threshold temperature (which may be pre-set for example), the temperature sensing device (not shown) is arranged to output a signal to the switch 170 to cause the switch 170 to open and thus disconnect the electrical supply to the atomiser 150. Alternatively, the temperature sensing device may be arranged to output a signal to the potentiometer to limit or reduce the voltage applied across the atomiser, should the sensed temperature reach a pre-defined threshold and thus obviate the requirement to cause the switch to open.

The device 100 further comprises an electrical port 185, such as a USB port, disposed in a side wall 113 of the housing for electrically coupling the device 100 with an external power source (not shown), such as a mains supply for recharging the battery arrangement 160.

Figure 2B:
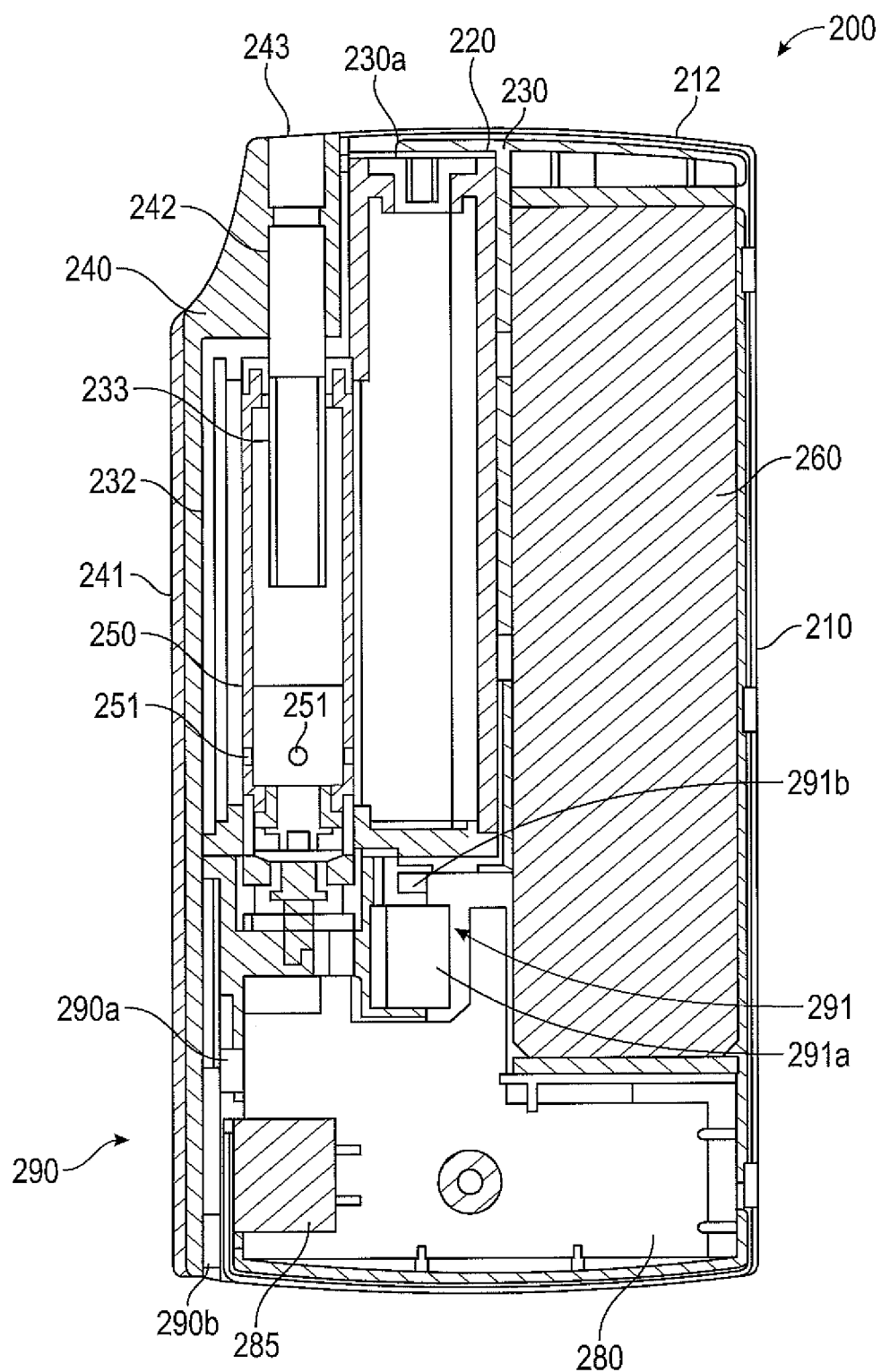
FIG. 2b is a schematic sectional view of a second embodiment of an electronic vapour generating device illustrated in FIG. 1, taken along line A-A of FIG. 1b.

Referring to FIGS. 1 and 2b of the drawings, there is illustrated an electronic vapour generating device 200 according to a second embodiment of the present invention. The device 200 of the second embodiment is substantially the same as the device 100 of the first embodiment and so like features have been referenced using the same numerals, but increased by 100. However, the device 200 of the second embodiment comprises a first and second switching assembly 290, 291 disposed in the electrical path between the battery arrangement 260 and the atomiser 250. In accordance with the device 200 of the second embodiment, the reconfiguration of the mouthpiece 240 between the stowed and operative configurations is arranged to reconfigure the operational state of the device from an "off" state to a "standby" state, rather than an "on" state. The first switching assembly 290 comprises a switch 290a, such as a reed switch, disposed proximate a base of the device 200, and a magnet 290b disposed upon the mouthpiece 240 at a proximal end thereof. The magnet 290b is arranged to move in accordance with the movement of the mouthpiece 240 and when the mouthpiece 240 is arranged in a stowed configuration, the magnet 290b is displaced from the reed switch 290a. However, when the mouthpiece 240 is configured in the operative configuration, the magnet 290b is arranged to align adjacent the reed switch 290a and in this configuration, the magnetic interaction between the magnet 290b and the switch 290a cause the switch 290a to reconfigure from an open to a closed configuration, to place the device 200 in a standby state.

The second switching assembly 291 comprises a pressure sensor 291a and a further switch (not shown). The pressure sensor 291a is arranged to detect a pressure within a sub-chamber 291b that is fluidly coupled with the mouthpiece 240. When a user inhales on the mouthpiece 240, the inhalation is detected by the pressure sensor 291a as a reduced pressure in the sub-chamber 291b and this detection is communicated as a signal to the further switch (not shown) to cause the further switch to reconfigure from an open state to a closed state and thus electrically couple the battery arrangement 260 with the atomiser 250 for generating the vapour. In this respect, with the device 200 placed in the standby state, the vapour is only generated at times when the user inhales on the mouthpiece 240.

Figure 4A:
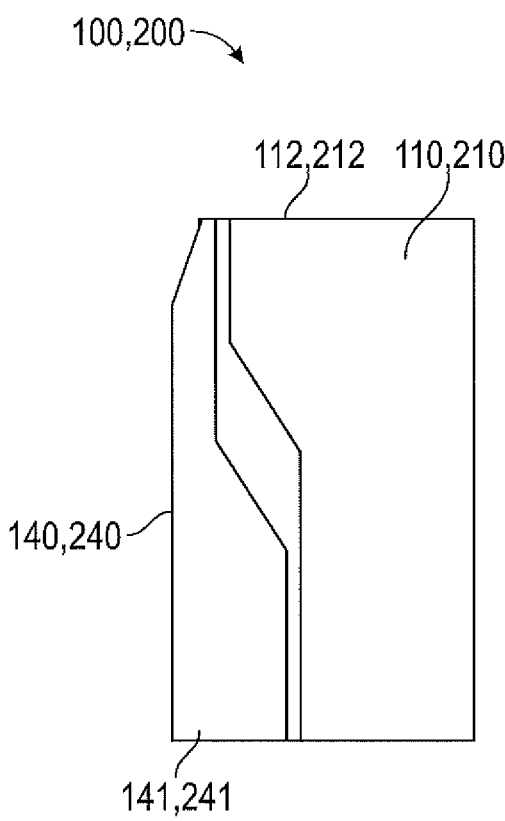
FIG. 4a is a front view of the electronic vapour generating device illustrated in FIG. 1, arranged in the stowed configuration.
Figure 4B:
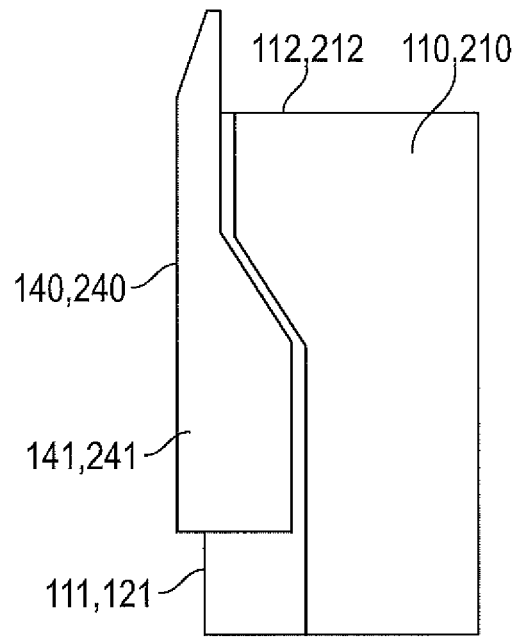
FIG. 4b is a front view of the electronic vapour generating device illustrated in FIG. 1, arranged in the operative configuration.
Figure 4C:
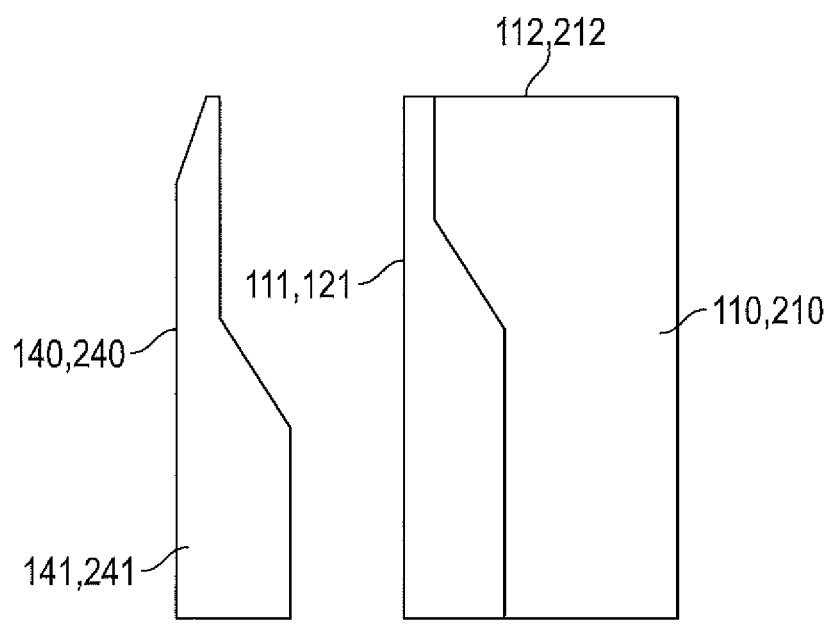
FIG. 4c is a front view of the electronic vapour generating device illustrated in FIG. 1, arranged in the release configuration.

Referring to FIG. 4 of the drawings, in use of the device 100, 200 of the first or second embodiment, the mouthpiece 140, 240 is configured to the release configuration so that the mouthpiece 140, 240 can be separated from the housing 110, 210 to enable a liquid filled cartridge 130, 230 to be inserted within the chamber 120, 220 within the housing 110, 210. The mouthpiece 140, 240 can then be coupled with the housing 110, 210, whereupon the atomiser 150, 250 becomes fluidly coupled with the receptacle 130, 230, and the mouthpiece 140, 240 is then reconfigured to the stowed configuration for storage for example.

When a user wishes to use the device 100 of the first embodiment for example, the mouthpiece 140 is first moved along the lateral side edge 111 of the housing 110 to reconfigure the mouthpiece 140 to the operative configuration and thus switch on the device. In accordance with the device of the first embodiment, this movement causes the distal end of the mouthpiece 140 to extend above the upper region 112 of the housing 110 and at the same time, the switch 170 is reconfigured to the second state to electrically couple the atomiser 150 with the battery arrangement 160. In the operative configuration, the atomiser 150 is arranged to draw liquid from the receptacle 131 and atomise the liquid to form a vapour, which can subsequently be drawn out from the mouthpiece 140 via the opening 143 by a user sucking at the distal end of the mouthpiece 140. Once the desired number of inhalations has been taken, the mouthpiece 140 can then be reconfigured to the stowed configuration, whereupon the switch 170 returns to the open state and thus electrically isolates the atomiser 150 from the battery arrangement 160 to switch off the device.

Upon reconfiguring the mouthpiece 140 to the operative configuration, the processor 182 is arranged to trigger the timer 181 to commence timing. The processor 182 subsequently monitors the time for which the mouthpiece 140 remains in the operative configuration and in the event that the mouthpiece 140 remains in the operative configuration for more than a predetermined time, such as a time in the interval of 5-10 seconds, then then processor 182 is arranged to electrically isolate the atomiser 150 from the battery arrangement 160. It is envisaged that this safety cut-off will prevent continuous unintended operation of the atomiser 150, should the mouthpiece inadvertently reconfigure to the operative configuration while in a users pocket or bag (not shown), for example. Moreover, it is to be appreciated, that the user is required to reconfigure the mouthpiece 140 to the stowed configuration and then back to the operative configuration, in order to reactivate the atomiser 150, should the user wish to take a prolonged series of inhalations lasting more than the predetermined time.

Alternatively during use of the device of the second embodiment, the reconfiguration of the mouthpiece 240 may instead cause the device 200 to be placed in a standby state, whereby vapour is only generated when a user inhales on the mouthpiece 240. The device 200 of the second embodiment thus avoids the requirement for a user to reconfigure the mouthpiece 240 between the operative and stowed configurations, between inhalations, for example.

When it is desired to replace the cartridge 130, 230 then the mouthpiece 140, 240 is reconfigured to the release configuration, whereupon the mouthpiece 140, 240 can be uncoupled from the housing 110, 210 to permit the cartridge 130, 230 to be removed from therewithin. A replacement cartridge 130, 230 can then be inserted and the mouthpiece 140, 240 recoupled with the housing 110, 210 and reconfigured to the operative or stowed configuration, for example.

From the foregoing therefore it is evident that the above described device provides for a more compact arrangement of generating a vapour.

The invention claimed is:

1. An electronic vapour generating device, the device comprising a housing defining a chamber for receiving a cartridge for holding a liquid for atomisation, and a power source for providing electrical power to an atomiser of the cartridge for atomising the liquid to generate a vapour,
the device further comprising an actuator which is reconfigurable between a first state in which the actuator is arranged to electrically isolate the atomiser from the power source and a second state for enabling the generation of the vapour,
the device further comprising a mouthpiece which is arranged to fluidly couple with the atomiser for communicating the vapour out from the device for inhalation by a user,
wherein the mouthpiece is reconfigurable between a stowed configuration and an operative configuration; and
wherein the reconfiguration of the mouthpiece between the stowed and operative configurations is arranged to reconfigure the actuator between the first state and the second state in which the actuator is electrically couplable with the power source, and,
wherein the actuator comprises a first switching assembly and a second switching assembly, wherein the first switching assembly is reconfigurable between an open and closed state in accordance with the reconfiguration of the mouthpiece between the stowed and operative configurations and the second switching assembly is reconfigurable between an open and closed state in dependence of a detected pressure within the mouthpiece,
the device further comprising a connecting pipe, wherein the mouthpiece is fluidly couplable to the atomiser via the connecting pipe which is sealingly and slidably couplable to a duct of the cartridge, the duct being arranged to communicatively couple with the atomiser for communicating vapour generated by the atomiser out from the cartridge, wherein the pipe is arranged to slide relative to the duct as the mouthpiece reconfigures between the stowed and operative configurations;
wherein the cartridge is removably insertable within the electronic vapour generating device, and wherein the cartridge comprises a receptacle for retaining the liquid for atomisation and an atomiser disposed within the receptacle for atomising the liquid;
wherein the atomiser comprises a plurality of channels formed in an outer wall thereof for communicating liquid disposed within the receptacle into the atomizer;
wherein the cartridge further comprises a sleeve which shrouds at least a portion of the atomiser, wherein the sleeve comprises a plurality of apertures which are alignable with the channels to permit the liquid to pass into the atomiser; and,
wherein the duct is coupled to the sleeve and the sleeve is arranged to move relative to the atomiser by manipulating the duct.

2. An electronic vapour generating device according to claim 1, wherein reconfiguration of the mouthpiece between the stowed and operative configuration is arranged to reconfigure the actuator between the first state and the second state in which the atomiser and power source are electrically coupled.

3. An electronic vapour generating device according to claim 1, wherein the mouthpiece is arranged to fluidly couple with the atomiser in the stowed and operative configurations.

4. An electronic vapour generating device according to claim 1, wherein a distal end of the mouthpiece is arranged to extend substantially flush with a periphery of the housing when the mouthpiece is arranged in the stowed configuration; and wherein the distal end of the mouthpiece is disposed away from the housing when the mouthpiece is arranged in the operative configuration.

5. An electronic vapour generating device according to claim 1, wherein the mouthpiece is reconfigurable between a stowed configuration, an operative configuration and a release configuration.

6. An electronic vapour generating device according to claim 1, wherein the atomiser and duct are orientated along a common axis.

7. An electronic vapour generating device according to claim 1, wherein the cartridge further comprises a docking station for providing electrical communication of the atomiser with a vapour generating device.

8. An electronic vapour generating device according to claim 1, further comprising an electrical port disposed in the housing for receiving an electrical connector, for electrically coupling the power source with an external power supply.

9. An electronic vapour generating device according to claim 1, further comprising a timer and a processor, wherein the processor is arranged to electrically isolate the atomiser from the power source following a pre-determined time.

10. An electronic vapour generating device according to claim 1, further comprising a slider mechanism for slidably coupling the mouthpiece to the housing, wherein the slider mechanism comprises biasing means for biasing the mouthpiece in the stowed configuration and separately the operative configuration, such that a user is required to overcome a threshold force in reconfiguring the mouthpiece between the stowed and operative configuration.

11. A cartridge for providing liquid for use in the electronic vapour generating device of claim 1, the cartridge comprising a receptacle for retaining the liquid and an atomiser disposed within the receptacle for atomising the liquid, the cartridge further comprising a duct fluidly coupled with the atomiser for communicating vapour generated within the atomiser out from the cartridge.

* * * * *